(12) United States Patent
Hong et al.

(10) Patent No.: US 9,752,127 B2
(45) Date of Patent: Sep. 5, 2017

(54) COMPOSITION FOR MAINTAINING CHROMOSOMAL STABILITY OF PLURIPOTENT STEM CELLS, CONTAINING SMALL-MOLECULE COMPOUNDS

(71) Applicant: KOREA UNIVERSITY RESEARCH AND BUSINESS FOUNDATION, Seoul (KR)

(72) Inventors: Sunghoi Hong, Seoul (KR); Hang-Soo Park, Seoul (KR); In-Sik Hwang, Seoul (KR); Kyung-A Choi, Gangwon-do (KR)

(73) Assignee: KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 0 days.

(21) Appl. No.: 14/906,547

(22) PCT Filed: Jul. 22, 2014

(86) PCT No.: PCT/KR2014/006642
§ 371 (c)(1),
(2) Date: Jan. 20, 2016

(87) PCT Pub. No.: WO2015/016523
PCT Pub. Date: Feb. 5, 2015

(65) Prior Publication Data
US 2016/0160183 A1 Jun. 9, 2016

(30) Foreign Application Priority Data
Jul. 27, 2013 (KR) ........................ 10-2013-0089205

(51) Int. Cl.
*C12N 5/074* (2010.01)

(52) U.S. Cl.
CPC ........ *C12N 5/0696* (2013.01); *C12N 2500/38* (2013.01); *C12N 2501/155* (2013.01); *C12N 2501/602* (2013.01); *C12N 2501/603* (2013.01); *C12N 2501/604* (2013.01); *C12N 2501/606* (2013.01); *C12N 2501/727* (2013.01)

(58) Field of Classification Search
CPC ........ C12N 2501/155; C12N 2501/606; C12N 2501/603; C12N 2501/602; C12N 2501/727; C12N 5/0696; C12N 2501/604
See application file for complete search history.

(56) References Cited

U.S. PATENT DOCUMENTS

| | | | |
|---|---|---|---|
| 2011/0104125 A1* | 5/2011 | Yu | A61K 35/545 424/93.7 |
| 2012/0009676 A1 | 1/2012 | Mack | |
| 2012/0028351 A1* | 2/2012 | Li | C12N 5/0606 435/350 |
| 2012/0301962 A1 | 11/2012 | Thomson et al. | |
| 2013/0040302 A1 | 2/2013 | Burke et al. | |

FOREIGN PATENT DOCUMENTS

| | | |
|---|---|---|
| KR | 10-2010-0101764 A | 9/2010 |
| KR | 10-2010-0124335 A | 11/2010 |
| KR | 10-2011-0094348 A | 8/2011 |
| KR | 10-2011-0124106 A | 11/2011 |
| KR | 10-2012-0094488 A | 8/2012 |
| KR | 10-2012-0121084 A | 11/2012 |
| KR | 10-1211610 B1 | 12/2012 |
| KR | 10-1211624 B1 | 12/2012 |
| WO | 2009117439 A2 | 9/2009 |
| WO | 2010077955 A1 | 7/2010 |
| WO | 2011050476 A1 | 5/2011 |
| WO | 2011082038 A2 | 7/2011 |
| WO | 2011123572 A1 | 10/2011 |
| WO | 2012019122 A2 | 2/2012 |
| WO | 2012087965 A2 | 6/2012 |

OTHER PUBLICATIONS

Classen et al., Mol. Reprod. Dev., 76(8): 722-732, 2009.*
Yu et al., Science, 318: 1917-1920, 2007.*
Lai et al., Cellular Reprogramming, 12(6): 641-653, 2010.*
Esteban et al., Cell Stem Cell, 6: 71-79, 2010.*
Esteban et al., Cell Stem Cell, 6: 71-79, 2010, supplemental materials.*
Li, W., et al., "Generation of human-induced pluripotent stem cells in the absence of exogenous Sox2", Stem Cells, Dec. 2009, pp. 2992-3000, vol. 27, No. 12.
Li, W., et al., "Generation of rat and human induced pluripotent stem cells by combining genetic reprogramming and chemical inhibitors", Cell Stem Cell, Dec. 18, 2008, pp. 16-19, vol. 4.
Lin, T., et al., "A chemical platform for improved induction of human iPSCs", Nature Methods, Oct. 18, 2009, pp. 805-808, vol. 6, No. 11.
Luo, L., et al., "Effects pf amtopxodants on the quality and genomic stability of induced pluripotent stem cells", Scientific Reports, Jan. 21, 2014, pp. 3779 (1-7), vol. 4.
Yuan, X., et al., "Brief report: combined chemical treatment enables Oct4-induced reprogramming from mouse embryonic fibroblasts", Stem Cells, Mar. 2011, pp. 593-553, vol. 29.

(Continued)

*Primary Examiner* — Thaian N Ton
(74) *Attorney, Agent, or Firm* — Hultquist, PLLC; Steven J. Hultquist

(57) ABSTRACT

The present invention relates to a composition for maintaining the chromosomal stability of pluripotent stem cells, which contains a small-molecule compound, and more particularly, to a composition for maintaining the chromosomal stability of induced pluripotent stem cells, which contains a ROCK inhibitor, a MEK inhibitor, an ALK5 inhibitor or an antioxidant, which is capable of inhibiting chromosomal structural and numerical mutations or DNA damage during induction of induced pluripotent stem cell and the subsequent culture of the cells. The small-molecule compound-containing composition for maintaining the chromosomal stability of induced pluripotent stem cells increases the reprogramming rate and efficiency during production of induced pluripotent stem cells and exhibits excellent effects on the inhibition of chromosomal structural and numerical mutations or DNA damage. Thus, the composition of the present invention is very useful for the development of induced pluripotent stem cell therapeutic agents having excellent chromosomal stability.

5 Claims, 12 Drawing Sheets

(56) References Cited

OTHER PUBLICATIONS

Zhu, S., et al., "Reprogramming of Human Primary Somatic Cells by OCT4 and Chemical Compounds", Cell Stem Cell, Dec. 3, 2010, pp. 651-655, vol. 7, No. 6.

Gross, B., et al., "Improved Generation of Patient-Specific Induced Pluripotent Stem Cells Using a Chemically-Defined and Matrigel-Based Approach", "Current Molecular Medicine", Jun. 1, 2013, pp. 765-776, vol. 13, No. 5.

\* cited by examiner

Table 1. The chromosomal mutation observed in 60 analyzed cells in chemical free and chemical treated mouse iPSCs

| | chromosome | | | | | | | | | | | | | | | | | | | | |
|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | X | Y |
| miPSC(-) | | | | | | | | | | | | | | | | | | | | | 20 |
| loss of 1 copy | | | | | | | | | | | | | | | | | | | | | 20 |
| gain of 1 copy | 1 | | | | | | | 6 | | 1 | 1 | | | 4 | | | | | | | |
| deletion | | | | | | | | | | | | | | 20 | | | | | | | |
| duplication | | | | 22 | | | | | | | | | | | | | | | | | |
| translocation | | | | | | | | | | | | | | | | | | 20 | 20 | | |
| miPSC(±) | | | | | | | | | | | | | | | | | | | | | |
| loss of 1 copy | | | | | | | | | | | | | | | | | | | | | 38 |
| gain of 1 copy | | | | | | | | | 20 | | 33 | | | | | | | | | | |
| deletion | | | | | | | | | | | | | | | | | | | | | |
| duplication | | | | | | | | | | | | | | | | | | | | | |
| translocation | | | | | | | | | | | | | | | | | | | | | |
| miPSC(+) | | | | | | | | | | | | | | | | | | | | | |
| loss of 1 copy | | | | | | | | | | | | | | | | | | | | | |
| gain of 1 copy | | | | | | | | | | | | | | | | | | | | | |
| deletion | | | | | | | | | | | | | | | | | | | | | |
| duplication | | | | | | | | | | | | | | | | | | | | | |
| translocation | | | | | | | | | | | | | | | | | | | | | |

FIG. 6B

Table 2. The chromosomal aneuploidy mutation observed in chemical free and chemical treated mouse iPSC lines

| | Ch.2 | Ch.8 | Ch.10 | Ch.11 | Ch.14 | Ch.Y | Mutation |
|---|---|---|---|---|---|---|---|
| miPSC(-) | Gain of 1 copy | Gain of 1 copy | Gain of 1 copy | Gain of 1 copy | Gain of 1 copy | Loss of 1 copy | O |
| miPSC(±) | | Gain of 1 copy | | Gain of 1 copy | | Loss of 1 copy | O |
| miPSC(+) | | | | | | | X |

FIG. 6C

Table 3. The chromosomal structure mutation observed in chemical free and chemical treated mouse iPSC lines

| | Ch.8 | Ch.14 | Ch.18 | Ch.19 | Mutation |
|---|---|---|---|---|---|
| miPSC(-) | Duplication | Deletion | t(18;19) | t(18;19) | O |
| miPSC(±) | | | | | X |
| miPSC(+) | | | | | X |

COMPOSITION FOR MAINTAINING CHROMOSOMAL STABILITY OF PLURIPOTENT STEM CELLS, CONTAINING SMALL-MOLECULE COMPOUNDS

CROSS-REFERENCE TO RELATED APPLICATIONS

This application is a U.S. national phase under the provisions of 35 U.S.C. §371 of International Patent Application No. PCT/KR14/06642 filed Jul. 22, 2014, which in turn claims priority of Korean Patent Application No. 10-2013-0089205 filed Jul. 27, 2013. The disclosures of such international patent application and Korean priority patent application are hereby incorporated herein by reference in their respective entireties, for all purposes.

TECHNICAL FIELD

The present invention relates to a composition for maintaining the chromosomal stability of pluripotent stem cells, which contains a small-molecule compound, and more particularly, to a composition for maintaining the chromosomal stability of induced pluripotent stem cells, which contains a ROCK inhibitor, a MEK inhibitor, an ALK5 inhibitor or an antioxidant, which is capable of inhibiting chromosomal structural and numerical mutations or DNA damage during the induction of induced pluripotent stem cell and the subsequent culture of the cells.

BACKGROUND ART

A technology for producing induced pluripotent stem cells is a technology of making cells similar to embryonic stem cells using animal somatic cells, and comprises culturing cells under specific culture conditions in the presence of four known reprogramming factors (Oct4, Klf4, Sox2, and cMyc). Induced pluripotent stem cells made by this method have advantages in that they can differentiate into all tissue-specific cells and can be used for cell therapy agents that pose no ethical problems, but these induced pluripotent stem cells have disadvantages in that they are produced with low efficiency, are difficult to guarantee their safety and are not completely similar to embryonic stem cells.

Since 2006 in which induced pluripotent stem cell technology was developed, many studies on this technology have been conducted and a variety of compositions resulting from these studies have been used to increase the efficiency with which induced pluripotent stem cells are produced. As a result, 23 papers have reported that the efficiency of production of induced pluripotent stem cells was successfully increased using specific composition, and 6 papers have reported that induced pluripotent stem cells were successfully produced even in the absence of one or more reprogramming factors.

Up to date, studies have been conducted mainly to increase the efficiency with which induced pluripotent stem cells are produced. However, when only the efficiency of production of induced pluripotent stem cells is increased in a state in which the verification of safety of induced pluripotent stem cells is insufficient, it does not appear that induced pluripotent stem cells are clinically applicable. Thus, in order to increase the clinical applicability of induced pluripotent stem cells, studies focused on increasing the safety of induced pluripotent stem cells are necessarily required, and a method of making induced pluripotent stem cells more similar to embryonic stem cells should be developed.

In prior art technologies related to the present invention, Korean Patent Registration No. 10-1211610 (Dec. 6, 2012) discloses a composition for inducing dedifferentiation from somatic cells to embryonic stem cell-like cells by use of Bmi1, a MEK inhibitor and a GSK inhibitor, and a method for producing embryonic stem cell-like cells using the composition. Korean Patent Registration No. 10-1211624 (Dec. 6, 2012) discloses a composition for inducing dedifferentiation from somatic cells to embryonic stem cell-like cells by use of Shh, a FGFR tyrosine kinase inhibitor, a MEK inhibitor and a GSK inhibitor, and a method for producing embryonic stem cell-like cells using the composition. In addition, Korean Patent Laid-Open Publication No. 10-2010-0101764 (Sep. 20, 2010), Korean Patent Laid-Open Publication No. 10-2011-0094348 (Aug. 23, 2011), Korean Patent Laid-Open Publication No. 10-2012-0094488 (Aug. 24, 2012), and Korean Patent Laid-Open Publication No. 10-2012-0121084 (Nov. 5, 2012) disclose a useful culture method and medium for producing and maintaining pluripotent stem cells, etc.

Several papers related to the background of the present invention have reported that treatment with compositions increases the efficiency with which induced pluripotent stem cells are produced, but whether this treatment with compositions can inhibit the mutation of induced pluripotent stem cells is not known. In particular, it has not been reported that the use of a composition containing a MEK inhibitor, an ALK5 inhibitor, a ROCK inhibitor or an antioxidant can inhibit mutation or DNA damage that is a problem occurring in the production of induced pluripotent stem cells, and thus can provide stable induced pluripotent stem cells.

Accordingly, the present inventors have found that a composition containing the ROCK inhibitor thiazovivin, the MEK inhibitor PD0325901, the ALK5 inhibitor SB431542 or the antioxidant L-ascorbic acid maintains chromosomal stability by inhibiting structural and numerical mutations or DNA damage in induced pluripotent stem cells, thereby completing the present invention.

PRIOR ART LITERATURE

Patent Documents

Patent Document 1: Korean Patent Registration No. 10-1211610 (Dec. 6, 2012)
Patent Document 2: Korean Patent Registration No. 10-1211624 (Dec. 6, 2012)
Patent Document 3: Korean Patent Laid-Open Publication No. 10-2010-0101764 (Sep. 20, 2010)
Patent Document 4: Korean Patent Laid-Open Publication No. 10-2011-0094348 (Aug. 23, 2011)
Patent Document 5: Korean Patent Laid-Open Publication No. 10-2012-0094488 (Aug. 24, 2012)
Patent Document 6: Korean Patent Laid-Open Publication No. 10-2012-0121084 (Nov. 5, 2012).

Non-Patent Documents

Non-Patent Document 1: Li, W., Wei, W., Zhu, S., Zhu, J., Shi, Y., Lin, T., Hao, E., Hayek, A., Deng, H., and Ding, S. (2009a). Generation of rat and human induced pluripotent stem cells by combining genetic reprogramming and chemical inhibitors. Cell Stem Cell 4, 16-19.

Non-Patent Document 2: Li, W., Zhou, H., Abujarour, R., Zhu, S., Young Joo, J., Lin, T., Hao, E., Scholer, H. R., Hayek, A., and Ding, S. (2009b). Generation of human-induced pluripotent stem cells in the absence of exogenous Sox2. Stem Cells 27, 2992-3000.

Non-Patent Document 3: Lin, T., Ambasudhan, R., Yuan, X., Li, W., Hilcove, S., Abujarour, R., Lin, X., Hahm, H. S., Hao, E., Hayek, A., et al. (2009). A chemical platform for improved induction of human iPSCs. Nat Methods 6, 805-808.

Non-Patent Document 4: Yuan, X., Wan, H., Zhao, X., Zhu, S., Zhou, Q., and Ding, S. (2011). Combined Chemical Treatment Enables Oct4-Induced Reprogramming from Mouse Embryonic Fibroblasts. Stem Cells.

Non-Patent Document 5: Zhu, S., Li, W., Zhou, H., Wei, W., Ambasudhan, R., Lin, T., Kim, J., Zhang, K., and Ding, S. (2010). Reprogramming of human primary somatic cells by OCT4 and chemical compounds. Cell Stem Cell 7, 651-655.

DISCLOSURE OF INVENTION

It is an object of the present invention to provide a composition for maintaining the chromosomal stability of induced pluripotent stem cells, which contains, as an active ingredient, at least one small-molecule compound selected from the group consisting of a ROCK inhibitor, a MEK inhibitor, an ALK5 inhibitor and an antioxidant.

Another object of the present invention is to provide a method for maintaining the chromosomal stability of induced pluripotent stem cells, the method comprising treating the induced pluripotent stem cells with then above-described composition, and a method for culturing induced pluripotent stem cells, the method comprising culturing the induced pluripotent stem cells with then above-described composition.

BRIEF DESCRIPTION OF THE DRAWINGS

FIGS. 6B and 6C show the results of analyzing representative karyotypes showing chromosomal numerical and structural abnormalities in induced pluripotent stem cells (miPSC(+)) cultured with a small-molecule compound-containing composition for a long period of time, induced pluripotent stem cells (miPSC(±)) treated with the composition in the initial culture stage after induction of reprogramming but not treated with the composition during subculture, and induced pluripotent stem cells (miPSC(−)) not treated with the composition, in order to confirm that the small-molecule compound-containing composition prevents chromosomal numerical and structural abnormalities.

BEST MODE FOR CARRYING OUT THE INVENTION

Figure 1A:
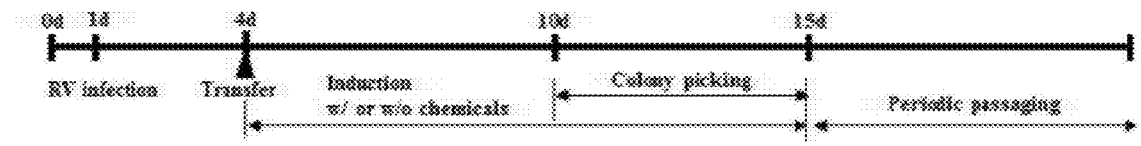
FIG. 1A schematically shows the overall experimental scheme that is used in a method for producing induced pluripotent stem cells.

Unless defined otherwise, all technical and scientific terms used herein have the same meaning as commonly understood by one of ordinary skill in the art to which the invention pertains. Generally, the nomenclature used herein and the experiment methods, which will be described below, are those well known and commonly employed in the art.

In one aspect, the present invention is directed to a composition for maintaining the chromosomal stability of induced pluripotent stem cells, which contains, as an active ingredient, at least one small-molecule compound selected from the group consisting of a ROCK inhibitor, a MEK inhibitor, an ALK5 inhibitor, and an antioxidant.

In the present invention, the ROCK (Rho-associated kinase) inhibitor serves to increase chromosomal stability, and is preferably selected from among thiazovivin, Y-27632, fasudil (HA-1077), hydroxyfasudil (HA-1100), H-1152, 3-(4-pyridyl)-1H-indole, N-(4-pyridyl)-N'-(2,4,6-trichlorophenyl)urea, aurothioglucose, and LY294002. Most preferably, the ROCK inhibitor is thiazovivin, but is not limited thereto.

In the present invention, the MEK (mitogen-activated protein kinase) inhibitor serves to increase chromosomal stability by inducing rapid reprogramming, and is preferably PD0325901 or U0126 (1,4-diamino-2,3-dicyano-1,4-bis[2-aminophenylthio]butadiene), more preferably PD0325901, but is not limited thereto. In addition to the above compounds, signaling inhibitors that inhibit all the metabolic processes of MEK and the expression of MEK may be used.

In the present invention, the ALK5 (activin receptor-like kinase-5) inhibitor serves to increase chromosomal stability by inducing rapid reprogramming, and is preferably A-83-01 or SB431542, more preferably SB431542, but is not limited thereto. In addition to the above compounds, signaling inhibitors that inhibit all the metabolic processes of ALK5 and the expression of ALK5 may be used.

In the present invention, the antioxidant is particularly limited in its kind, but may preferably be at least one selected from the group consisting of vitamin E, vitamin A, vitamin C, etc., oxothiazolidine, N-acetylcysteine, TEMPO, SOD (superoxide dismutase), glutathione peroxidase, scavenger oxygen, hydrogen peroxide, lipoic oxide radical, a hydroxy radical, a metal binding protein, selenium, reduced glutathione, beta-carotene, flavonoids, sesamol, gallic acid derivatives, Ajowan, oryzanol, resveratrol, catechin, lecithin, cephalin, sulfhydrls (SRH), citric acid, ascorbic acid, catalase, BHA, BHT, PG, NDGA, hydroquinone, catechol, and DPPD (N, Ndiphenyl-pp-phenylene-diamine), more preferably, L-ascorbic acid. Particularly, the L-ascorbic acid can increase chromosomal stability improving the cell viability through the antioxidant activity.

The small-molecule compound in the composition of the present invention may be prepared by artificial synthesis, or may be a commercially synthesized product. When a commercially synthesized product is used, it is preferably added to a medium after dissolution in DMSO. In a specific example of the present invention, it was added to DMEM medium.

In the present invention, the stem cells are preferably induced pluripotent stem cells induced by one or more genes selected from the group consisting of Oct4, Klf4, Sox2, and cMyc.

The present invention is characterized in that chromosomal stability is maintained by inhibiting chromosomal structural and numerical mutations or DNA damage.

As used herein, the term "pluripotent" or "pluripotency" refers to cells with the ability to give rise to progeny that can undergo differentiation, under appropriate conditions, into cell types that collectively exhibit characteristics associated with cell lineages from the three germ layers (endoderm, mesoderm, and ectoderm). Pluripotent stem cells or induced pluripotent stem cells can contribute to many or all tissues of an adult animal. A standard art-accepted test, such as the ability to form a teratoma in 8-12 week old SCID mice, can be used to establish the pluripotency of a cell population, however identification of various pluripotent stem cell characteristics can also be used to detect pluripotent cells, however identification of various pluripotent stem cell characteristics can also be used to detect pluripotent cells. Cell pluripotency is a continuum, ranging from the completely pluripotent cell that can form every cell of the embryo proper, e.g., embryonic stem cells and induced pluripotent stem cells, to the incompletely or partially pluripotent cell that can form cells of all three germ layers but that may not exhibit all the characteristics of completely pluripotent cells, such as, for example, germline transmission or the ability to generate a whole organism. In some embodiments, expression of pluripotency genes or pluripotency markers as discussed elsewhere herein can be used to assess the pluripotency of a cell.

As used herein, the term "pluripotent stem cells" refers to cells having pluripotent stem cell characteristics. The pluripotent stem cells are pluripotent reprogrammed stem cells, induced pluripotent stem cells, or embryonic stem cells, and are preferably pluripotent reprogrammed stem cells.

As used herein, "pluripotent stem cell characteristics" refers to characteristics of a cell that distinguish pluripotent stem cells from other cells. The ability to give rise to progeny that can undergo differentiation, under the appropriate conditions, into cell types that collectively demonstrate characteristics associated with cell lineages from all of the three germinal layers (endoderm, mesoderm, and ectoderm) is a pluripotent stem cell characteristic. Mouse pluripotent stem cells express at least some, and optionally all, of markers, including SSEA1, Oct4, Klf4, Sox2, Rex1, and Nanog. Cell morphologies associated with pluripotent stem cells are also pluripotent stem cell characteristics.

In a specific example of the present invention, in order to examine whether a composition containing a small-molecule compound increases the reprogramming rate and efficiency of induced pluripotent stem cells, induced pluripotent stem cells were produced by introducing reprogramming factors (Oct4, Klf4, Sox2, and cMyc) into mouse tail tip fibroblasts using a retrovirus. At the same time, the reprogramming rate and efficiency were measured by comparing the time point and number of induced pluripotent stem cell colonies produced, between a cell group (miPSC(+)) cultured in the presence of the small-molecule compound-containing composition and a cell group (miPSC(−)) cultured in the absence of the small-molecule compound-containing composition. As a result, it was found that the reprogramming rate was increased in the presence of the small-molecule compound-containing composition of the present invention, and the results of counting the induced pluripotent stem cell colonies produced indicated that the efficiency of production of the colonies was increased.

Induced pluripotent stem cells produced using the small-molecule compound-containing composition are characterized in that their abilities to proliferate and maintain pluripotency are closer to those of embryonic stem cells. It was observed that there was little or no unnecessary differentiation in the induced pluripotent stem cells produced using the composition of the present invention and that the expression levels of pluripotency genes such as Nanog, Klf4 and Zfp296, which are expressed in embryonic stem cells, were increased.

In addition, it was shown that the induced pluripotent stem cells produced using the small-molecule compound-containing composition of the present invention had differentiation ability closer to that of embryonic stem cells, and were capable of extodermal differentiation into the neuron-specific expression protein Tuj1, mesodermal differentiation into the mycocyte-specific expression protein Desmin, and endodermal differentiation into primitive mesenchymal cell-specific expression protein AFP. Finally, it was found that the induced pluripotent stem cells produced using the composition of the present invention formed functional neurons with higher efficiency in inducing differentiation into functional neurons.

The small-molecule compound-containing composition of the present invention is characterized in that it can inhibit the numerical and structural mutations of cellular chromosomes caused by a rapid cellular change during the production of induced pluripotent stem cells. Analysis of chromosomal karyotypes indicated that various chromosomal structural mutations such as duplication, deletion and translocation occurred in induced pluripotent stem cells not treated with the composition, but chromosomal structural mutations were not found in induced pluripotent stem cells treated with the small-molecule compound-containing composition.

Furthermore, the small-molecule compound-containing composition of the present invention is characterized in that it can inhibit cellular DNA damage caused by a rapid cellular change during the production of induced pluripotent stem cells. Immunofluorescent staining of the γH2AX protein indicated that DNA damage occurred in up to about 20% of induced pluripotent stem cells not treated with the composition, but DNA damage occurred in only less than 5% of induced pluripotent stem cells treated with the small-molecule compound-containing composition, which is similar to that in normal cells. Particularly, the small-molecule compound used in the present invention could inhibit DNA damage even when it was used alone, and other small-molecule compounds known to increase reprogramming efficiency did not show this DNA damage inhibitory effect.

Because chromosomal mutation or DNA damage as described above can reduce the efficiency of maintenance and differentiation of cells and has a potential risk of inducing abnormal differentiation to develop into cancer cells, it is considered that the composition of the present invention is also consistent with the purpose of producing induced pluripotent stem cells for safe cell therapy.

Taking the foregoing together, the small-molecule compound-containing composition according to the present invention can prevent the mutation or DNA damage in cellular chromosomes caused by a rapid cellular change during reprogramming. In addition, the composition of the present invention induces somatic cell reprogramming to occur faster, increases the efficiency of reprogramming, and increases the expression levels of genes that are expressed specifically in embryonic stem cells. Thus, the present invention can provide induced pluripotent stem cells having proliferation and differentiation capabilities more similar to those of embryonic stem cells.

Thus, unlike the prior art documents that mention only the increase in the reprogramming efficiency, the small-molecule compound-containing composition of the present invention, which can also increase chromosomal stability, has the effects of increasing the efficiency and safety of induced pluripotent stem cells when these cells are used in clinical therapy, and is highly valuable not only as a raw material for producing cell therapeutic agents, but also as a material for chromosomal mutation studies.

In another aspect, the present invention is directed to a method for maintaining the chromosomal stability of induced pluripotent stem cells, the method comprising treating the induced pluripotent stem cells with a composition for maintaining the chromosomal stability of induced pluripotent stem cells, which contains, as an active ingredient, at least one small-molecule compound selected from the group consisting of a ROCK inhibitor, a MEK inhibitor, an ALK5 inhibitor, and an antioxidant.

In the present invention, the composition is preferably added in an initial stage in which somatic cell reprogramming is induced. Because the initial stage means a period ranging from the introduction of one or more genes selected from Oct4, Klf4, Sox2 and cMyc to the culture-induced formation of colonies, the composition is most preferably added within 4 days after gene introduction, which is the initial stage in which reprogramming is induced. In addition, the composition is preferably added in a long-term culture stage in which induced pluripotent stem cells formed after induction of reprogramming are maintained.

In the present invention, the composition may also contain each of a MEK inhibitor, an ALK5 inhibitor, a ROCK inhibitor and an antioxidant, and preferably contains a combination of two or more of these inhibitors and the antioxidant. Most preferably, the composition contains a combination of all of these inhibitors and the antioxidant.

In still another aspect, the present invention is directed to a method for culturing induced pluripotent stem cells, the method comprising culturing the induced pluripotent stem cells with a composition for maintaining the chromosomal stability of induced pluripotent stem cells, which contains, as an active ingredient, at least one small-molecule compound selected from the group consisting of a ROCK inhibitor, a MEK inhibitor, an ALK5 inhibitor, and an antioxidant.

In the present invention, the method for culturing induced pluripotent stem cells may further comprise culturing the induced pluripotent stem cells under a feeder cell-free condition. If the induced pluripotent stem cells are stabilized, these cells may be cultured on a culture dish coated only with gelatin under a feeder cell-free condition. If the cells are cultured in a feeder cell-free condition, unnecessary differentiation will occur in the absence of the composition of the present invention, making it difficult to make the cells showing a uniform morphology, whereas the use of the composition of the present invention can inhibit unnecessary differentiation, making it possible to maintain the induced pluripotent stem cells in a more stable and effective manner.

As a medium for culture of induced pluripotent stem cells in the present invention, any basal medium known in the art may be used without limitation. The basal medium that is used in the present invention may be a synthetic basal medium or a commercially available basal medium. Examples of the commercially available basal medium include Dulbecco's modified eagle's medium (DMEM), minimal essential medium (MEM), basal medium eagle (BME), RPMI 1640, F-10, F-12, a-minimal essential medium (a-MEM), Glasgow's minimal essential medium (G-MEM), and Isocove's modified Dulbecco's medium, but is not limited thereto. The commercially available basal medium may be DMEM. In addition, the basal medium preferably include 10% (v/v) horse serum. In a specific example of the present invention, the induced pluripotent stem cells were cultured in the DMEM medium.

The present invention can provide a method of producing induced pluripotent stem cells, which have proliferation and differentiation capabilities more similar to those of embryonic stem cells, using the small-molecule compound-containing composition of the present invention.

As described above, the present invention is directed to a method of maintaining the chromosomal stability of induced pluripotent stem cells using the small-molecule compound-containing composition and a method of culturing induced pluripotent stem cells using the small-molecule compound-containing composition. More specifically, the present invention is directed to the novel use of a composition containing as an active ingredient a small-molecule compound that increases the efficiency with which induced pluripotent stem cells are produced. According to the present invention, induced pluripotent stem cells, produced by introducing four reprogramming factors (Oct4, Sox2, Klf4, and c-Myc) into mouse tail tip fibroblasts and then culturing the fibroblasts in a medium containing a small-molecule compound (a ROCK inhibitor, a MEK inhibitor, an ALK5 inhibitor, or an antioxidant) as an active ingredient, can be produced in a rapid and efficient manner and can also inhibit chromosomal mutations and DNA damage. Such results can be very effectively used not only in the production of safe induced pluripotent stem cells that can be used in clinical applications in future, but also in the development of various cell therapeutic agents after differentiation of these cells into various functional cells. In other words, the present invention can be effectively used as a core technology for developing stem cell lines for cell therapy, which can treat various incurable diseases.

In the above description, the description has been made centering on the culture of the induced pluripotent stem cell, but it will be obvious to those skilled in the art to which the present invention pertains that the composition of the present invention comprising a small molecule compound an active ingredient has the effects of maintaining pluripotency and inhibiting chromosomal mutations or DNA damage, and can be utilized using a known technique.

EXAMPLES

Hereinafter, the present invention will be described in further detail with reference to examples. It will be obvious to a person having ordinary skill in the art that these examples are illustrative purposes only and are not to be construed to limit the scope of the present invention. Thus, the substantial scope of the present invention will be defined by the appended claims and equivalents thereof.

Example 1: Construction of Retrovirus Comprising Reprogramming Factor for Induction of Reprogramming In order to construct a retrovirus capable of delivering genes of four reprogramming factors (Oct4, Klf4, Sox2, and cMyc), a pMXs vector plasmid purchased from Addgene was used. 293GPG cells for constructing retrovirus were cultured in a 100-mm cell culture dish so as to grow to a confluence of about 80%, and the plasmid was introduced into the 293GPG cells using Lipofectamin 2000 (Invitrogen) according to the enclosed guidelines. After 48 hours, 5 ml of retrovirus secreted as the supernatant of the cell culture was collected everyday for 2 weeks and stored at −80° C. until use. The retrovirus was mixed with a medium containing 2-4 µg/ml of polybrene, and the cells were cultured in the medium for 4-5 hours to infect the cells with the retrovirus and deliver the genes into the cells.

Example 2: Production of Induced Pluripotent Stem Cells Using Composition Containing Small-Molecule Compound 2-1: Combination and Addition of Small-Molecule Compounds To produce induced pluripotent stem cells using small-molecule compounds, a MEK inhibitor, an ALK5 inhibitor, a ROCK inhibitor and an antioxidant were added to a medium composition, and cells were cultured in the medium composition. Specifically, as the small-molecule compounds, the MEK inhibitor PD0325901, the ALK5 inhibitor SB431542, the ROCK inhibitor thiazovivin and the antioxidant L-ascorbic acid were used alone or in combination. Each of the small-molecule compounds was a powdery product purchased from manufacturing companies such as Stemgent, Cayman and Sigma. Herein, the MEK inhibitor PD0325901 was dissolved in dimethyl sulfoxide (DMSO) at a concentration of 0.5 mM and stored as a 1000-fold concentrate at a temperature of −20° C., and the ALK5 inhibitor SB431542 was dissolved in dimethyl sulfoxide (DMSO) at a concentration of 2 mM and stored as a 1000-fold concentrate at a temperature of −20° C. The ROCK inhibitor thiazovivin was dissolved in dimethyl sulfoxide (DMSO) at a concentration of 0.5 mM and stored as a 1000-fold concentrate at a temperature of −20° C., and the antioxidant L-ascorbic acid was dissolved in triple distilled water at a concentration of 200 mM and stored as a 1000-fold concentrate at a temperature of −20° C. Each of the small-molecule compounds was used as an additive to a medium in a culture process for producing induced pluripotent stem cells or maintaining the chromosomal stability of induced pluripotent stem cells. Herein, the final concentrations of the small-molecule compounds in the medium were 0.5 µM for PD0325901, 2 µM for SB431542, 0.5 µM for thiazovivin, and 200 µM for L-ascorbic acid.

2-2: Production of Induced Pluripotent Stem Cells

Reprogramming factors were introduced into mouse tail tip fibroblasts using retrovirus, thereby obtaining induced pluripotent stem cells. Specifically, about 50,000-100,000 mouse fibroblasts at about passage 2-3 were cultured in a 100-mm cell culture dish, and after the culture, the cells were infected with the retrovirus comprising the plasmid containing four reprogramming factors (Oct4, Klf4, Sox2, and cMyc) at an MOI of 2 or more.

The cells infected with the virus were further cultured for about two days, and then treated with 0.05% trypsin-EDTA 2- for 3 minutes to isolate single cells. The isolated cells were cultured on feeder cells grown on a 6-well cell culture dish coated with 0.1% gelatin. As the feeder cells, mouse fibroblasts whose division was inhibited by mitomycin were used. The small-molecule compound-containing composition prepared in Example 2-1 was added to a medium for culture of mouse embryonic stem cells, and the fibroblasts introduced with the reprogramming factors were cultured in the medium under the conditions of 5% carbon dioxide and temperature of 37° C. The basal medium composition for culture of mouse stem cells, used in this Example, was composed of DMEM high-glucose medium (GIBCO) supplemented with 2 mM L-glutamine, 10 mM beta-mercaptoethanol, 0.1 mM MEM NEAA, 500 unit/ml ESGRO (LIF), 10% horse serum, and the antibiotic Pen/strep.

2-3: Culture of Induced Pluripotent Stem Cells

Figure 1B:
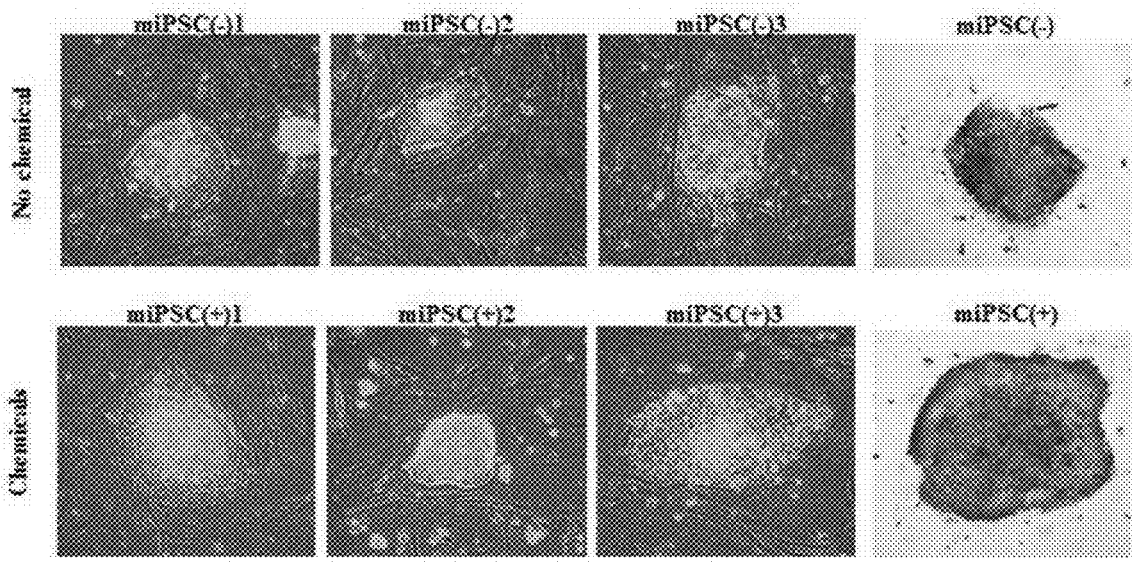
FIG. 1B depicts photographs showing that treatment with a composition containing a small-molecule composition and non-treatment with the composition provide induced pluripotent stem cells having a typical morphology.
Figure 1C:
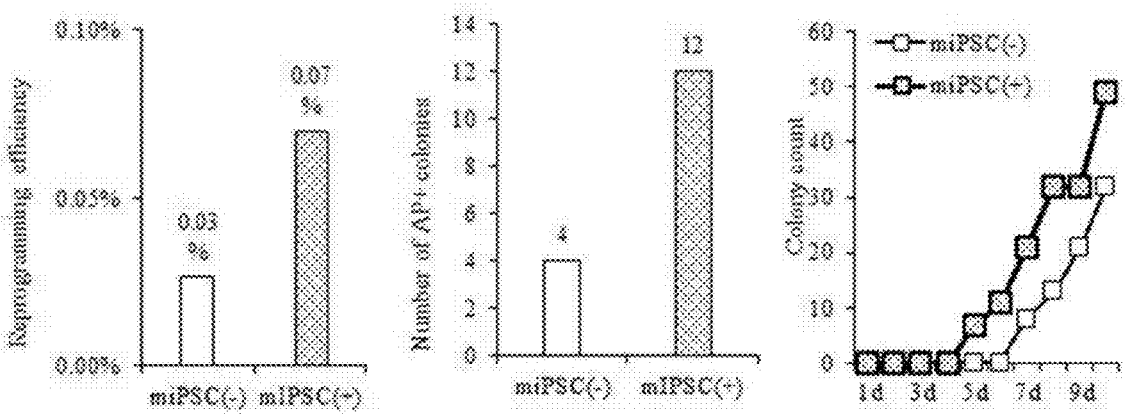
FIG. 1C is a graph showing a comparison of the reprogramming efficiency and rate between induced pluripotent stem cells treated with a small-molecule compound-containing composition and induced pluripotent stem cells not treated with the composition.

After about 1 week of culture, it was observed that induced pluripotent stem cell colonies having a morphology similar to that of embryonic stem cells were formed on the feeder cells (FIG. 1B). In order to examine whether the formed induced pluripotent stem cell colonies have characteristics similar to those of embryonic stem cells, AP staining was performed. The results of the AP staining indicated that induced pluripotent stem cell colonies were observed, which were stained red and positive for the staining (FIG. 1B). The AP staining was performed using a test kit (Stemgent) according to the attached guideline. In addition, it was shown that the small-molecule compound-containing composition of the present invention increased the reprogramming rate and efficiency (FIG. 1C).

The produced induced pluripotent stem cell colonies were physically detached using a glass pipette and were cultured on fresh feeder cells. It was found that, when the induced pluripotent stem cells were stabilized, these cells could be cultured on a culture dish coated only with gelatin without feeder cells.

Figure 2A:
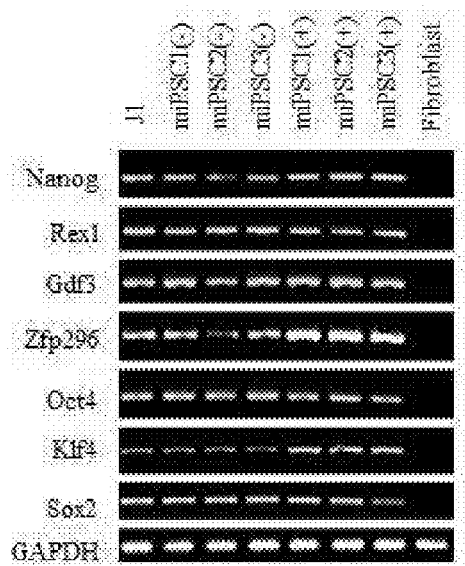
FIGS. 2A and 2B are photographs showing the results of RT-PCR and fluorescent staining analysis performed to analyze the expressions of pluripotency genes and proteins in induced pluripotent stem cells treated with a small-molecule compound-containing composition and induced pluripotent stem cells not treated with the composition.
Figure 2B:
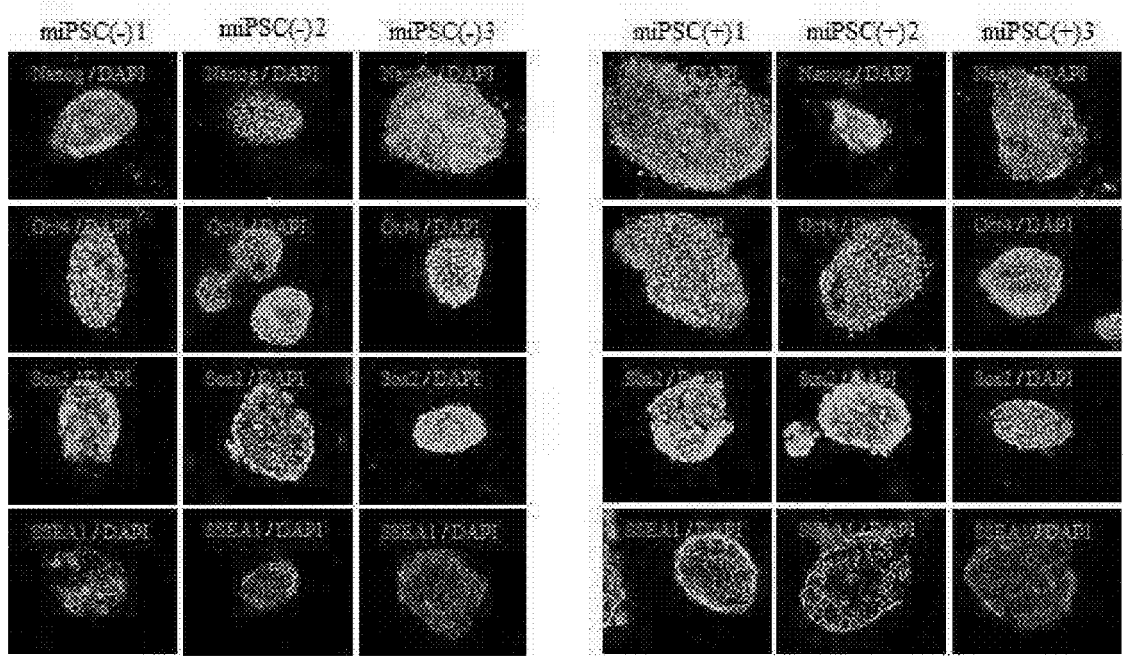

Example 3: Confirmation of Pluripotency of Induced Pluripotent Stem Cells By RT-PCR and Immunofluorescent Staining—Verification of Produced Induced Pluripotent Stem Cells For RT-PCR, the induced pluripotent stem cells were treated with 0.05% trypsin-EDTA for 2-3 minutes to isolate single cells, and the isolated cells were centrifuged. The precipitate was transferred into a 1.5-ml tube, and RNA was extracted therefrom. The cellular RNA was isolated using TRI reagent. 3 µg of the RNA was converted to cDNA using reverse transcriptase and oligo (dT), and the cDNA of interest was amplified by PCR using primers. The PCR products were electrophoresed to examine the expression level of the gene of interest. The results of the PCR indicated that the constructed induced pluripotent stem cell lines all expressed pluripotency genes, including Oct4, Klf4, Sox2, Nanog and Rex1 (FIG. 2A). For immunofluorescent staining, the cells being cultured in a multi-well culture dish were washed with PBS, and then fixed with 4% para-formaldehyde solution at room temperature for 1 hour or at 4° C. overnight. The fixed cells were treated with 0.1% triton-X solution for 5 minutes to puncture the cell membrane, after which the cells were blocked with 10% normal donkey serum, and then incubated with primary antibody. The results of immunofluorescent staining indicated that pluripotency markers, including Oct4, Klf4, Sox2, cMyc and SSEA1, were expressed in all the induced pluripotent stem cells (FIG. 2B).

Example 4: Examination of Differentiation Ability of Induced Pluripotent Stem Cells—Verification of Produced Induced Pluripotent Stem Cells 4-1: Differentiation of Induced Pluripotent Stem Cells In order to examine the ability of the produced induced pluripotent stem cells to differentiate, all the cell lines were treated with trypsin-EDTA to isolate single cells, and then the formation of embryonic bodies (EBs) were induced. To allow the induced pluripotent stem cells to differentiate into embryonic bodies (EBs), the induced pluripotent stem cells were suspension-cultured in the absence of LIF that inhibits differentiation of the induced pluripotent stem cells. Specifically, the induced pluripotent stem cells being cultured were washed with PBS, and then treated with 0.05% trypsin-EDTA for 2-3 minutes to isolate single cells. The isolated cells were suspension-cultured for 4 days with DMEM high-glucose medium (GIBCO) supplemented with 2 mM L-glutamine, 10 mM beta-mercaptoethanol, 0.1 mM MEM NEAA, 10% fetal bovine serum (FBS) and the antibiotic Pen/strep, in a culture dish for bacterial culture to which cells do not adhere, thereby obtaining suspended EBs.

Figure 3A:
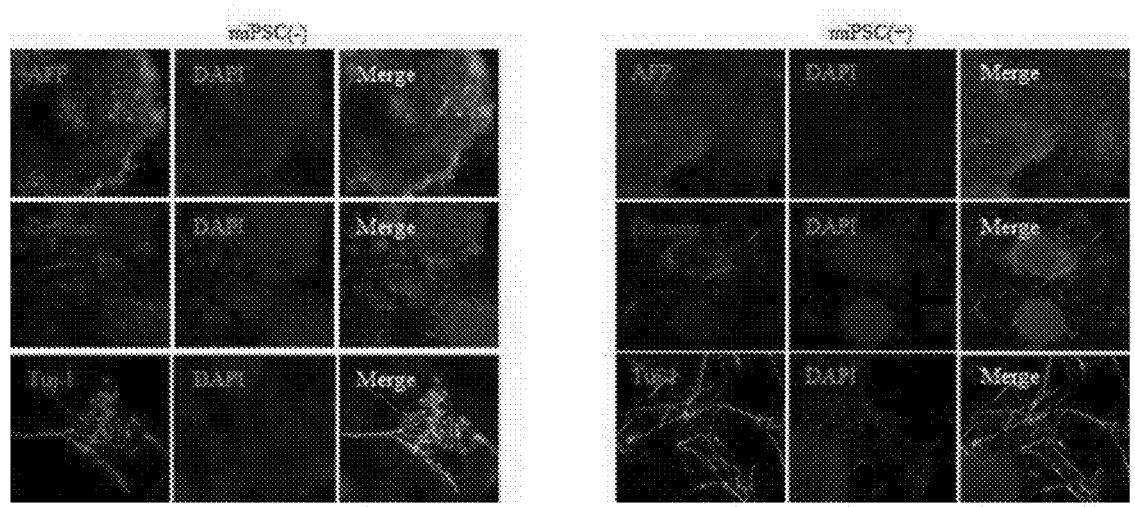
FIG. 3A depicts fluorescence staining images showing the abilities of induced pluripotent stem cells, treated with a small-molecule compound-containing composition, and induced pluripotent stem cells not treated with the composition, to differentiate into three germ layers.

The obtained EBs were transferred into a cell culture dish and adherent-cultured therein, and the extodermal, endodermal and mesodermal differentiated cells formed were observed by immunofluorescent staining. The results of immunofluorescent staining indicated that all the constructed induced pluripotent stem cells had the ability to normally differentiate and could differentiate into all the three germ layers (FIG. 3A).

4-2: Teratoma Production

Figure 3B:
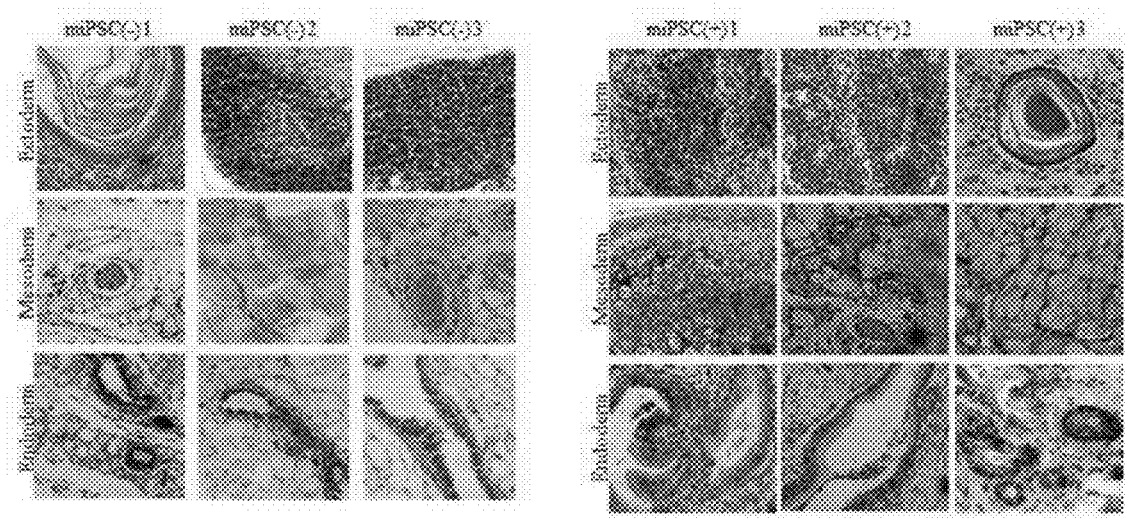
FIG. 3B depicts photographs showing the results of histological examination performed to confirm differentiation into three germ layers, after formation of tumors in immunodeficient mice by a teratoma formation experiment, in order to confirm the in vivo differentiation abilities of induced pluripotent stem cells treated with a small-molecule compound-containing composition and induced pluripotent stem cells not treated with the composition.

In order to examine the ability of induced pluripotent stem cells to differentiate in vivo, a teratoma production method using immunodeficient mice was used. In other words, in order to examine whether a teratoma is produced by transplantation of induced pluripotent stem cells, a method of transplanting induced pluripotent stem cells subcutaneously into immunodeficient SCID mice (BALB/c nu) was used. Specifically, the induced pluripotent stem cells being cultured were washed with PBS and treated with trypsin-EDTA to isolate single cells, and then 1,000,000 cells were diluted with 0.1 ml of a medium and the mixture was mixed uniformly with 0.1 ml of BD Matrigel matrix and injected subcutaneously into the side of 5-10-week-old SCID mice. After injection, whether a teratoma was formed in the mice was observed while the mice were kept for about 8-10 weeks. The produced teratoma was extracted and subjected to histological analysis using H&E staining, and differentiation into three germ layers was observed with a microscope. The results of histological analysis of the teratomas indicated that all the induced pluripotent stem cell lines normally produced teratomas and that structures corresponding to ectoderm, endoderm and mesoderm were found in the teratomas (FIG. 3B).

Example 5: Examination of the Effect of Small-Molecule Compound-Containing Composition on the Stable Maintenance of Induced Pluripotent Stem Cells In order to examine the effect of the small-molecule compound-containing composition on the induced pluripotent stem cells constructed and cultured in Example 2, morphological analysis, analysis of proliferation rate, and analysis of gene expression levels were performed. In order to examine the effect of the small-molecule compound-containing composition on the morphological and visual changes in the induced pluripotent stem cells, the induced pluripotent stem cells (miPSC(−)) not treated with the composition, and the induced pluripotent stem cells (miPSC(+)) constructed using the composition were compared with each other under a condition with feeder cells and a feeder cell-free condition.

Figure 4A:
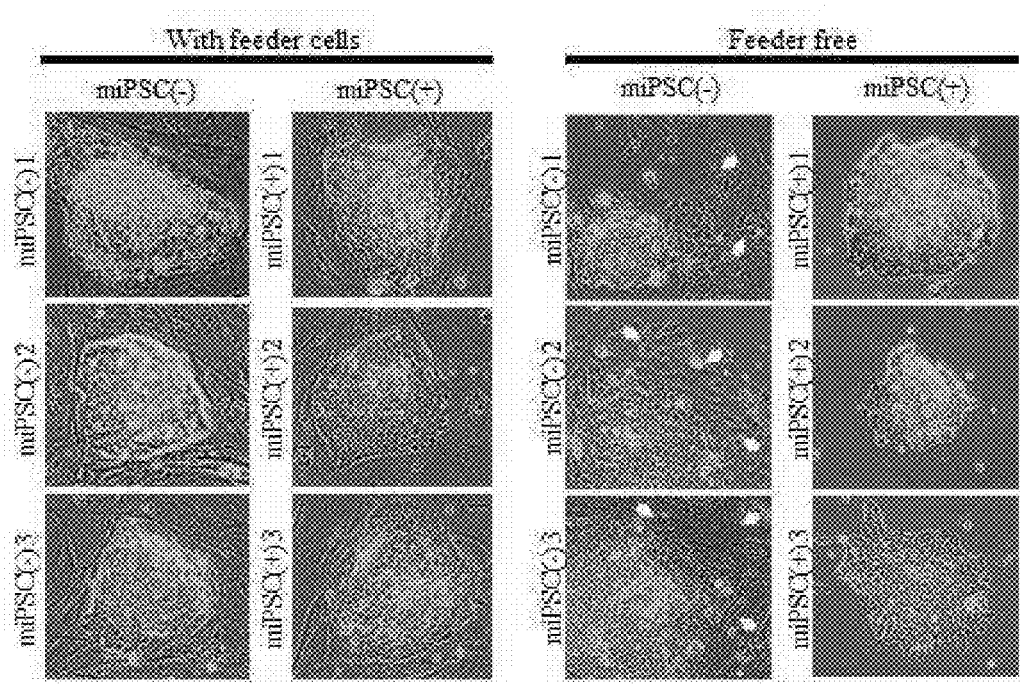
FIG. 4A depicts images showing that induced pluripotent stem cells treated with a small-molecule compound-containing composition can be maintained in a more stable manner without causing unnecessary differentiation when the stem cells are cultured without feeder cells.

In the condition with feeder cells, there was no great problem in maintaining the morphology and characteristics of the cells, even when the small-molecule compound-containing composition was not used, but in the feeder cell-free condition, unnecessary differentiation occurred when the small molecule-containing composition was not used, making it difficult to make the cells showing a uniform morphology. However, when the small-molecule compound-containing composition was used, the composition inhibited unnecessary differentiation, making it possible to maintain the induced pluripotent stem cells in a more stable and effective manner (FIG. 4A).

Figure 4B:
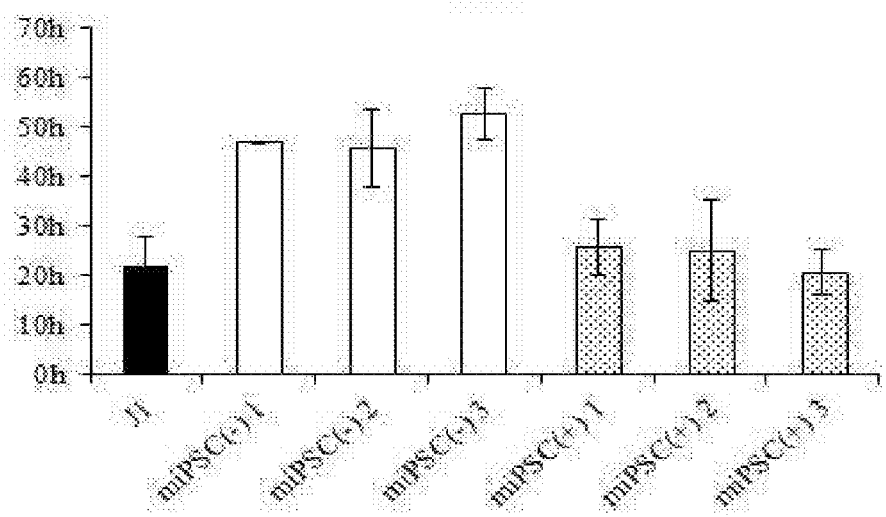
FIGS. 4B and 4C are graphs showing the results of cell counting and PCR performed to examine increases in the proliferation ability of induced pluripotent stem cells treated with a small-molecule compound-containing composition and the expression levels of pluripotency genes in the induced pluripotent stem cells.

In order to examine the effect of the small-molecule compound-containing composition on the proliferation rate of the induced pluripotent stem cells, the proliferation rate of the induced pluripotent stem cells produced using the composition and the proliferation rate of the induced pluripotent stem cells produced using the composition were compared with each other. The same number of different types of cells were cultured for the same time, and the cells were counted and compared. As a result, it was shown that the time required for the cells to divide once was shorter in the induced pluripotent stem cells treated with the small-molecule compound-containing composition, and this shorter time was almost similar to that for embryonic stem cells (FIG. 4B).

Figure 4C:
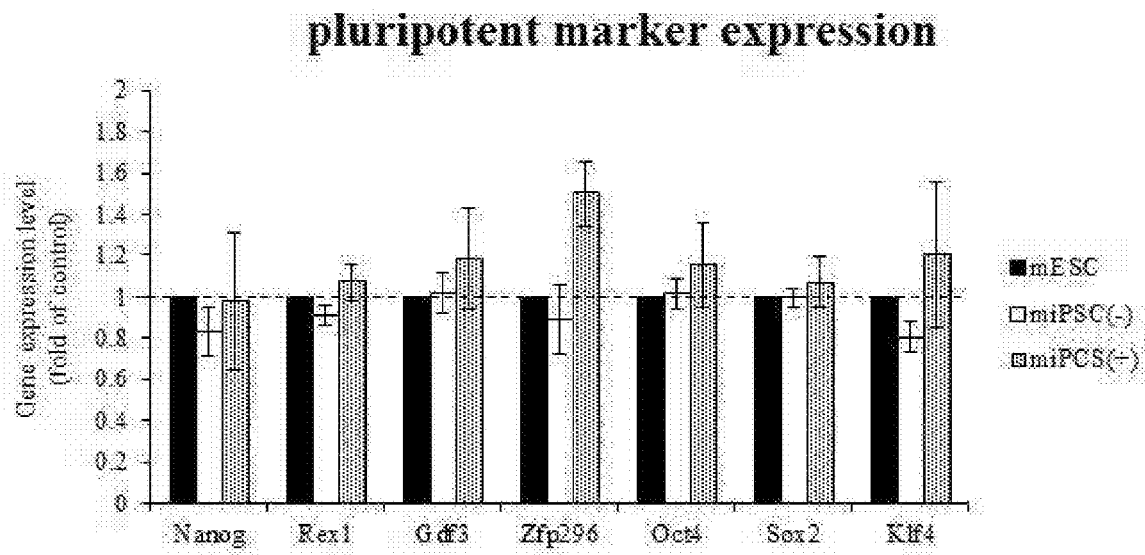

Finally, in order to examine the effect of the small-molecule compound-containing composition on the expression levels of pluripotency genes during the maintenance of the induced pluripotent stem cells, the expressions of pluripotency genes examined in Example 2 were quantitatively analyzed. As a result, it was shown that the expression levels of most pluripotency genes in the induced pluripotent stem cells produced using the small-molecule compound-containing composition were slightly higher (FIG. 4C).

Example 6: Examination of the Effect of Small-Molecule Compound-Containing Composition on Increase in Differentiation Ability of Induced Pluripotent Stem Cells In order to examine the effect of the small-molecule compound-containing composition on the differentiation ability of the induced pluripotent stem cells during the differentiation of the induced pluripotent stem cells constructed and cultured in Example 2, the efficiency of differentiation into the three germ layers, the volume of teratomas produced and the efficiency of formation of EBs were compared between the induced pluripotent stem cells not treated with the composition and the induced pluripotent stem cells produced using the composition.

Figure 5A:
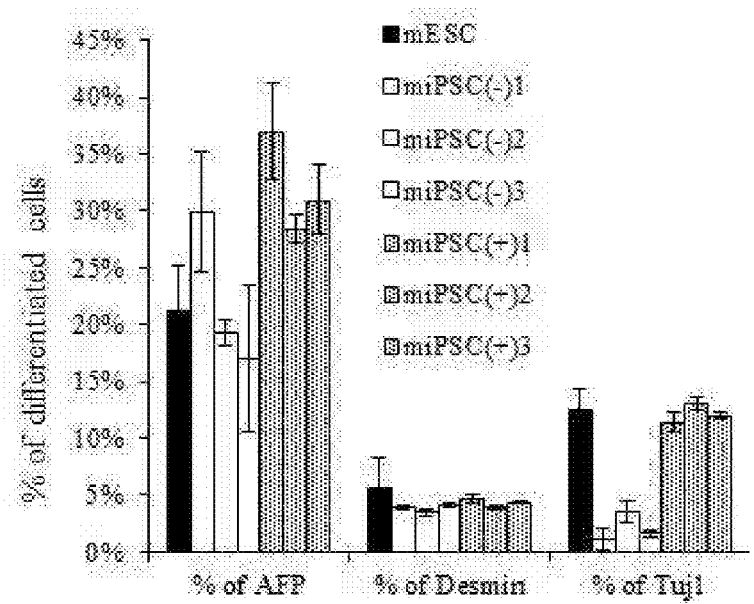
FIGS. 5A to 5D show the results of cell counting, a comparison of the volume of tumors formed in immunodeficient mice, and a comparison of the ability to form EBs (embryonic bodies), by fluorescent staining of induced pluripotent stem cells treated with a small-molecule compound-containing composition and induced pluripotent stem cells not treated with the composition, performed to confirm that the ability of the induced pluripotent stem cells to differentiate is increased.
Figure 5B:
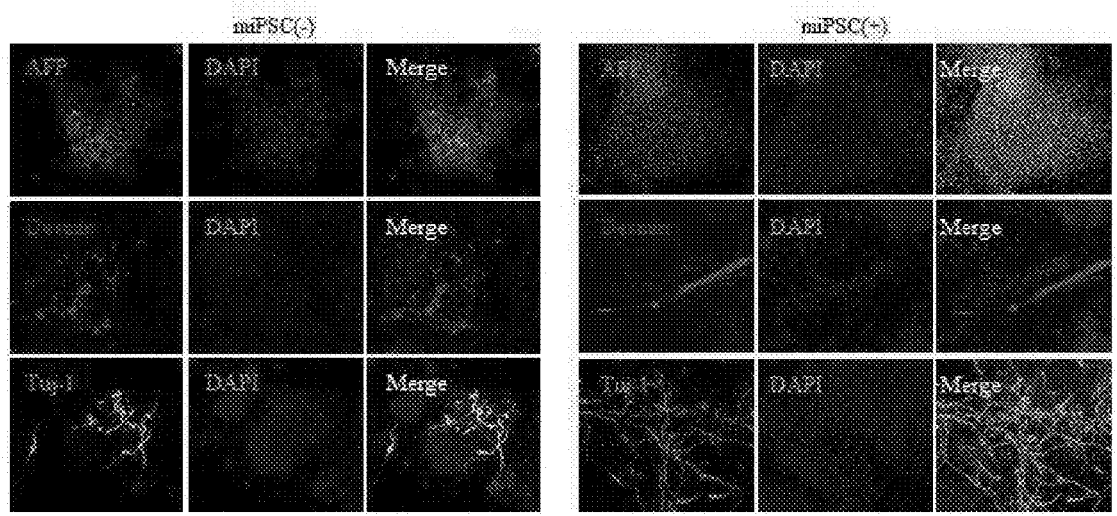

The cells that differentiated into ectoderm, endoderm and mesoderm were observed by immunofluorescent straining, and the number of the cells expressing each of the markers was counted, thereby measuring the efficiency of differentiation into the three germ layers. As a result, it was shown that the cell line constructed using the small-molecule compound-containing composition showed higher efficiency of extodermal differentiation compared to the cell line not treated with the composition. This suggests that the small-molecule compound-containing composition increases the differentiation ability of induced pluripotent stem cells (FIGS. 5a and 5b).

Figure 5C:
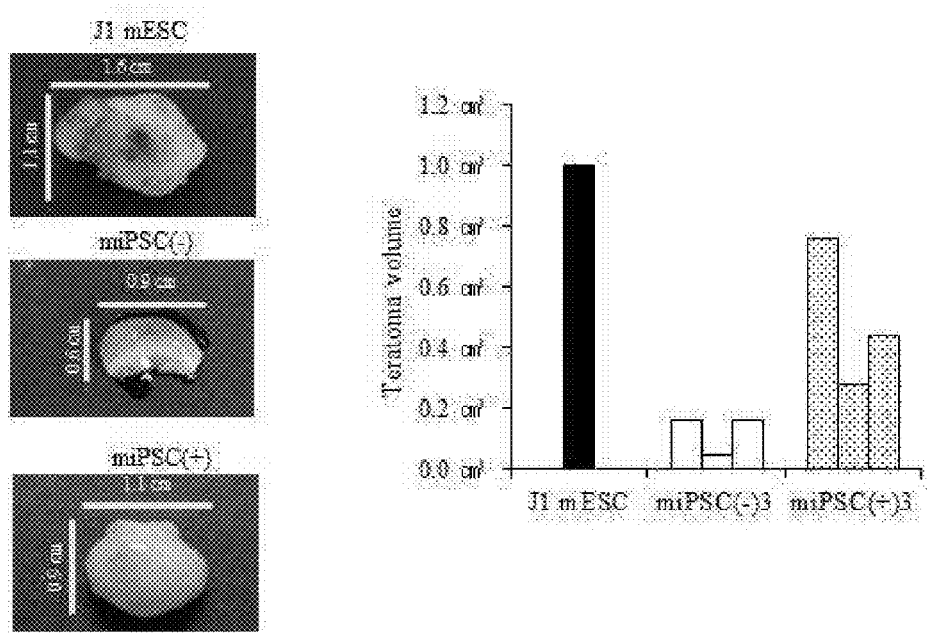

The volumes of teratomas produced in vivo were compared. As a result, it was shown that the volume of the teratoma produced from the cell line not treated with the small-molecule compound-containing composition was very small, whereas the volume of the teratoma produced from the cell line constructed using the small-molecule compound-containing composition was similar to the volume of a teratoma produced from embryonic stem cells, and the composition of the present invention also increased the ability of the induced pluripotent stem cells to differentiate in vivo (FIG. 5C).

Figures 5D, 6A:
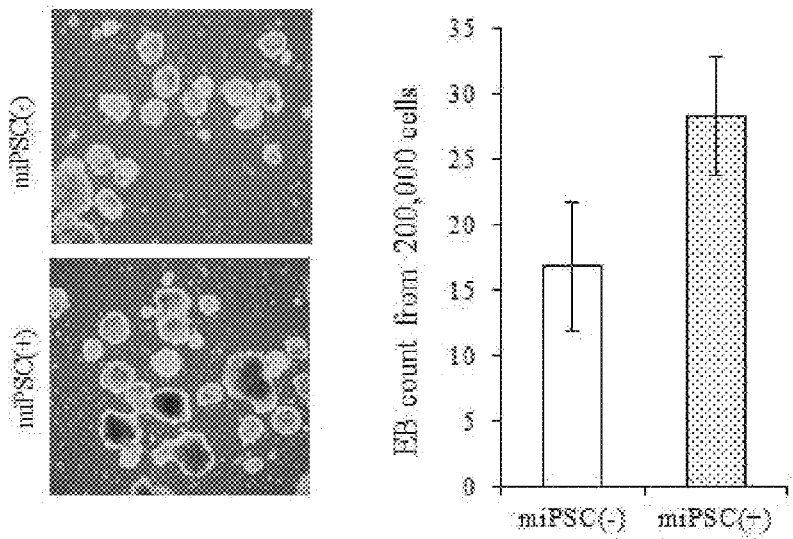
FIG. 6A is a table showing the resulting of comparing the frequency of chromosomal abnormalities between induced pluripotent stem cells (miPSC(+)) cultured with a small-molecule compound-containing composition for a long period of time, induced pluripotent stem cells (miPSC(±)) treated with the composition in the initial culture stage after induction of reprogramming but not treated with the composition during subculture, and induced pluripotent stem cells (miPSC(−)) not treated with the composition, in order to confirm that the small-molecule compound-containing composition prevents chromosomal structural abnormalities.
Figure 6D:
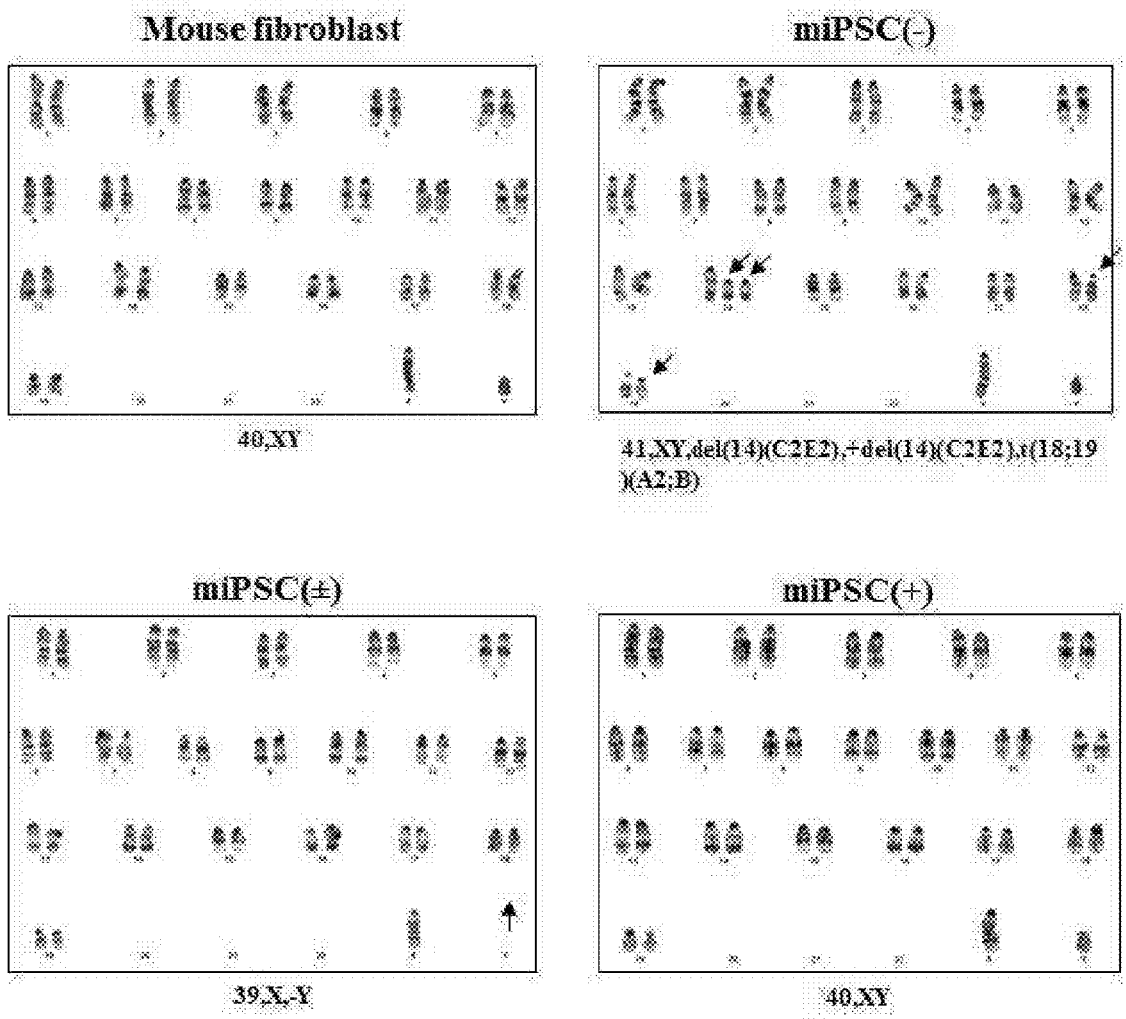
FIG. 6D shows the results of comparatively analyzing total karyotypes in induced pluripotent stem cells (miPSC (+)) cultured with a small-molecule compound-containing composition for a long period of time, induced pluripotent stem cells (miPSC(±)) treated with the composition in the initial culture stage after induction of reprogramming but not treated with the composition during subculture, and induced pluripotent stem cells (miPSC(−)) not treated with the composition, in order to confirm that the small-molecule compound-containing composition prevents chromosomal abnormalities.

The number of EBs formed from the induced pluripotent stem cells not treated with the small-molecule compound-containing composition and the number of EBs formed from the induced pluripotent stem cells produced using the small-molecule compound-containing composition were measured and compared with each other. As a result, it was shown that the small-molecule compound-containing composition also increased the efficiency of formation of EBs (FIG. 5D).

Example 7: Examination of the Effect of Small-Molecule Compound-Containing Composition on Inhibition of Chromosomal Mutations in Induced Pluripotent Stem Cells In order to examine whether the small-molecule compound-containing composition increases genetic stability during induction of induced pluripotent stem cells, initial culture of the cells after the induction process, and long-term maintenance and culture of the cells, whether chromosomal mutations occurred and the frequency of chromosomal mutations were examined by analyzing the karyotypes of the induced pluripotent stem cells not treated with the composition and the induced pluripotent stem cells produced using the composition. All the cells were cultured for a long period of time such that mutations would naturally occur, and the chromosomes thereof were analyzed by a general karyotype analysis process.

In order to examine the effect of the small-molecule compound-containing composition, the cell line not treated with the composition was compared with the cell line treated with the composition. As a result, it was shown that chromosomal structural and numerical mutations occurred in the induced pluripotent stem cells not treated with the small-molecule compound-containing composition, whereas chromosomal mutations did not occur in the induced pluripotent stem cells treated with the small-molecule compound-containing composition. In addition, it could be seen that, in the long-term culture process after the initial culture process in which reprogramming was induced using the composition, chromosomal structural mutations did not occur in the induced pluripotent stem cells (miPSC(±)) not treated with the composition, but mutations in chromosome number occurred. This suggests that the small-molecule compound-containing composition can inhibit chromosomal mutations in induced pluripotent stem cells and also has an effective ability to inhibit mutations that can occur in the reprogramming induction process, the initial culture stage and the subsequent process of maintaining and culturing cells for a long period of time (FIGS. 6A to 6D).

Example 8: Examination of the Effect of Small-Molecule Compound-Containing Composition on Inhibition of DNA Damage In another analysis method to examine whether the small-molecule compound-containing composition increases genetic stability during induction of induced pluripotent stem cells, initial culture of the cells after the induction process, and long-term maintenance and culture of the cells, the degree of DNA damage was analyzed.

Figure 7A:
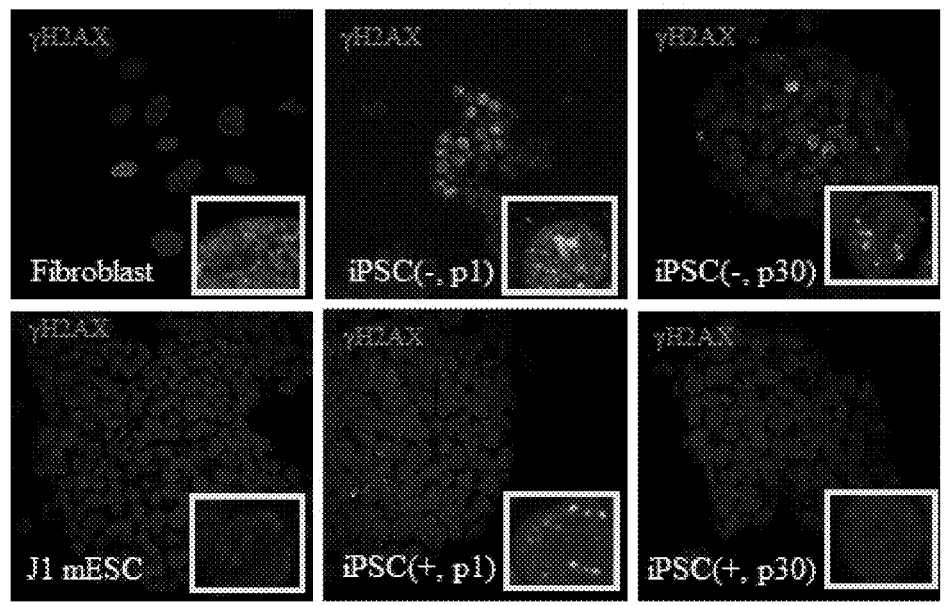
FIGS. 7A and 7B show the results of comparing DNA damage prevention by analyzing the DNA damage marker γH2AX protein in the p1 and p30 of induced pluripotent stem cells (miPSC(+)) treated with a small-molecule compound-containing composition and the p1 and p30 of induced pluripotent stem cells (miPSC(−)) not treated with the composition.

Using fibroblasts and mouse embryonic stem cells before reprogramming as a positive control, the difference in the degree of DNA damage between initial passage (−, p1) cells and long-term passage (−, p30) cells of induced pluripotent stem cells not treated with the composition, and initial passage (+, p1) cells and long-term passage (+, p30) cells of induced pluripotent stem cells produced using the composition, was examined. The degree of DNA damage was analyzed based on the presence or absence of the γH2AX protein that is produced by DNA damage, and the protein of interest was stained and analyzed using a green fluorescence-labeled antibody by immunofluorescent staining (FIG. 7A).

In order to analyze the effect of the small-molecule compound-containing composition in more detail, the ratio of generation of the γH2AX protein between the cell line not treated with the composition and the cell line treated with the composition was analyzed.

Figure 7B:
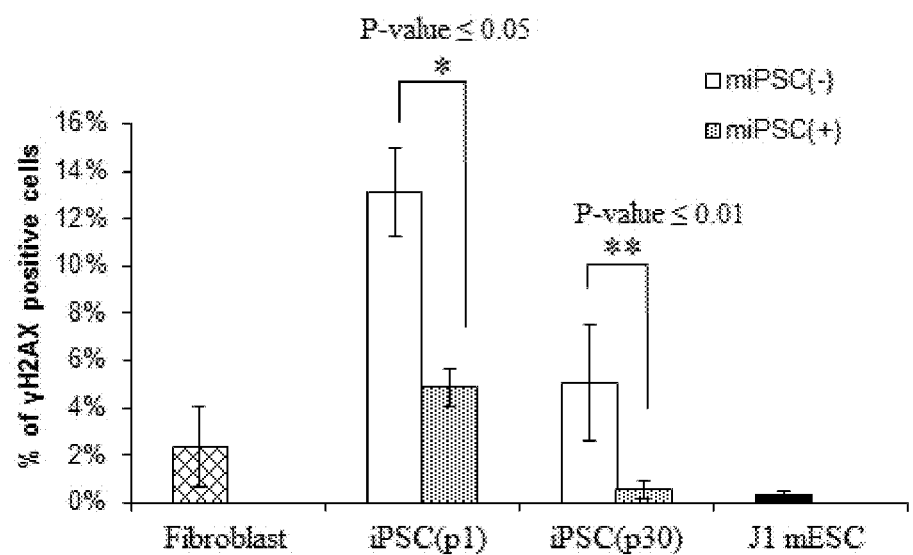
Figure 7C:
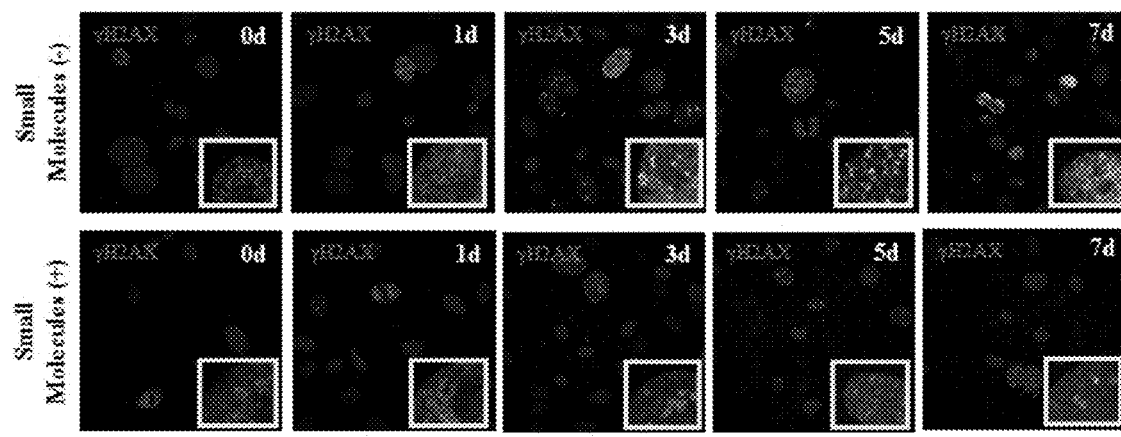
FIGS. 7C and 7D show the results of analyzing the DNA damage marker γH2AX protein for initial 7 days after the induction of reprogramming of induced pluripotent stem cells (miPSC(+)) treated with a small-molecule compound-containing composition and the p1 and p30 of induced pluripotent stem cells (miPSC(−)) not treated with the composition, in order to confirm that the medium composition prevents DNA damage from occurring in the initial reprogramming stage.
Figure 7D:
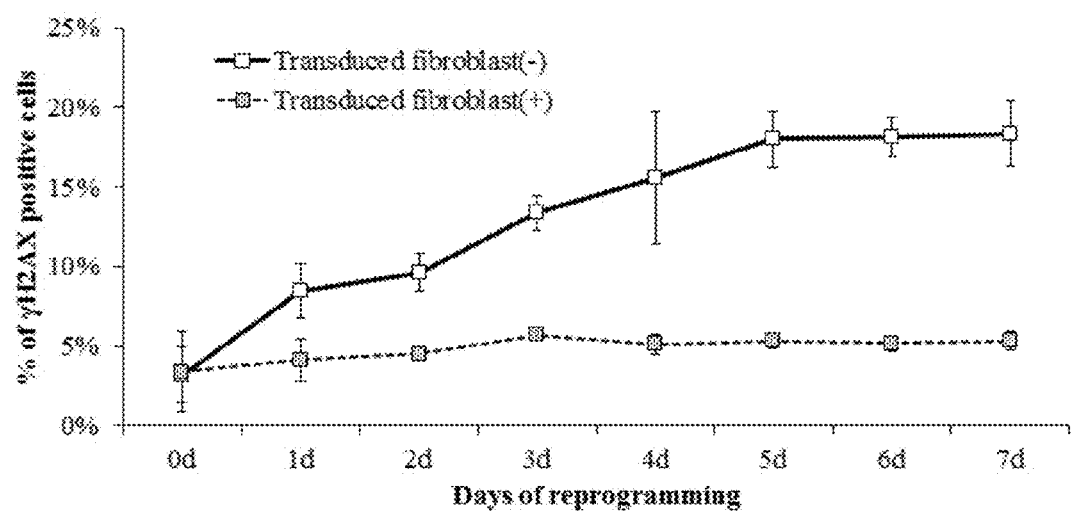
Figure 7E:
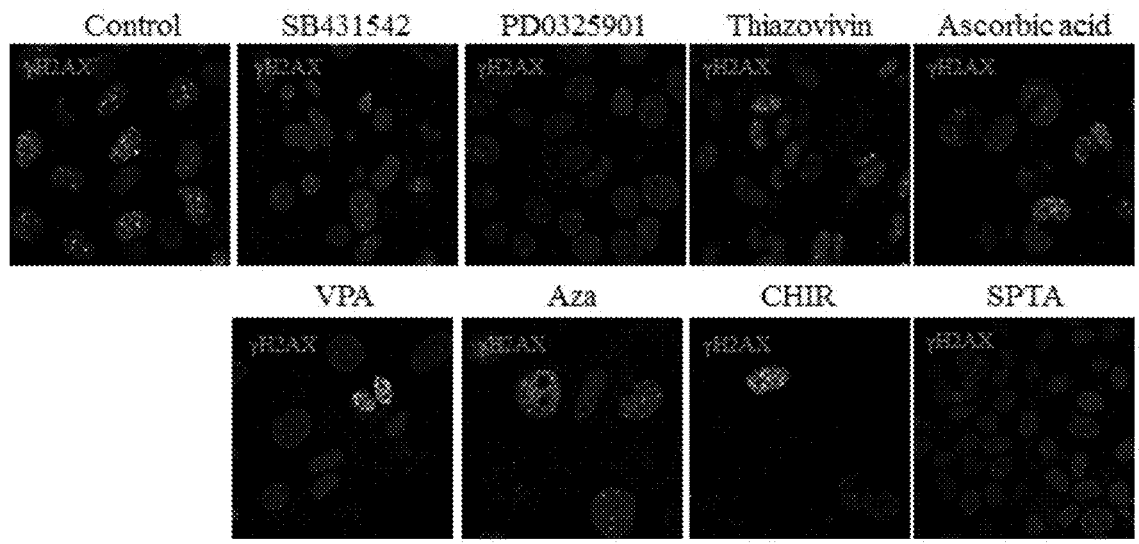
FIGS. 7E and 7F show the results of detecting and comparatively analyzing the DNA damage marker γH2AX protein at 5 days after the induction of reprogramming under a condition (SPTA) in which a combination of all small-molecule compounds of the present invention were used, a condition in which each of the small-molecule compounds was used, and a condition in which other small-molecule compounds known to increase reprogramming efficiency were used.
Figure 7F:
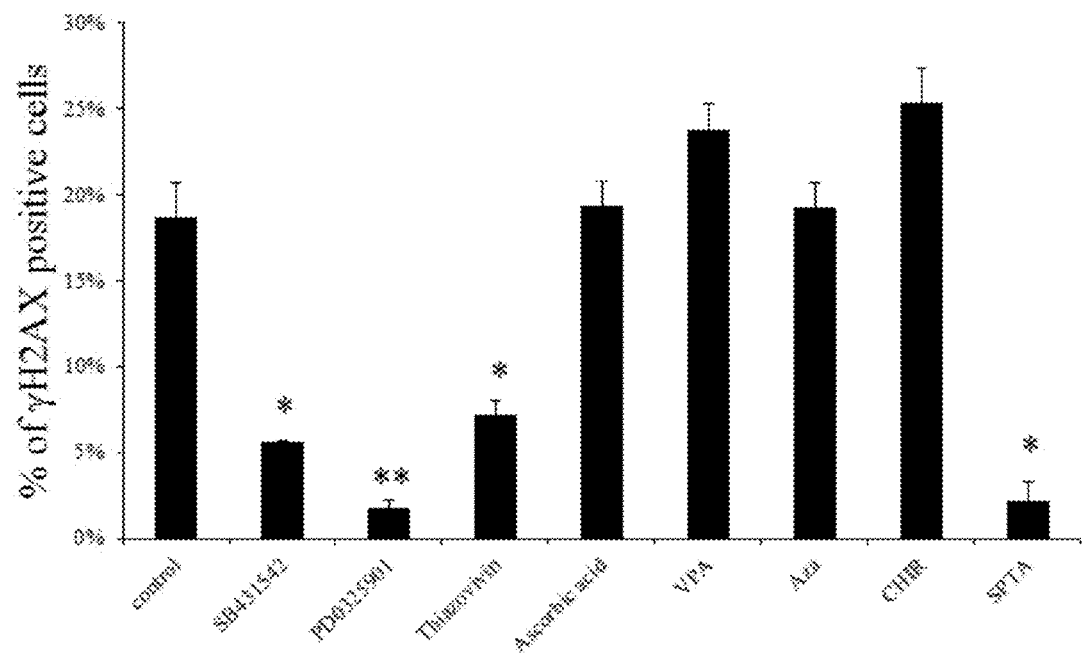

As a result, it was shown that, in the induced pluripotent stem cells not treated with the composition, about 13% of the initial passage (p1) cells and about 5% of the long-term passage (p30) cells underwent DNA damage, whereas in the induced pluripotent stem cells treated with the composition, only about 5% of the initial passage (p1) cells and only less than about 1% of the long-term passage (p30) cells underwent DNA damage. This indicates that the use of the small-molecule compound during reprogramming or long-term culture after reprogramming shows a DNA state similar to that of normal fibroblasts or normal embryonic stem cells before reprogramming, suggesting that the composition of the present invention can inhibit DNA damage in induced pluripotent stem cells to a level similar to that in normal stem cells (FIG. 7B).

INDUSTRIAL APPLICABILITY

As described above, the small-molecule compound-containing composition for maintaining the chromosomal stability of induced pluripotent stem cells according to the present invention increases the reprogramming rate and efficiency during production of induced pluripotent stem cells and exhibits excellent effects on the inhibition of chromosomal structural and numerical mutations or DNA damage. Thus, the composition of the present invention is very useful for the development of induced pluripotent stem cell therapeutic agents having excellent chromosomal stability.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A method for maintaining the chromosomal stability of induced pluripotent stem cells by inhibiting DNA damage, the method comprising:
    treating the induced pluripotent stem cells with a composition consisting of SB431542, PD0325901, thiazovivin and L-ascorbic acid,
    wherein the induced pluripotent stem cells are generated by introduction of genes consisting of Oct4, Klf4, Sox2, and cMyc.

2. The method of claim 1, wherein the composition is added during induction of reprogramming.

3. The method of claim 1, wherein the composition is added after induction of reprogramming.

4. A method for culturing induced pluripotent stem cells, the method comprising:
    culturing the induced pluripotent stem cells in a composition that contains, as an active ingredient, a small-molecule compound consisting of SB431542, PD0325901, thiazovivin and L-ascorbic acid,
    wherein the induced pluripotent stem cells are generated by introduction of genes consisting of Oct4, Klf4, Sox2, and cMyc.

5. The method of claim 4, further comprising culturing the induced pluripotent stem cells under a feeder cell-free condition.

* * * * *